United States Patent [19]

Catiis et al.

[11] Patent Number: 5,236,696
[45] Date of Patent: Aug. 17, 1993

[54] CONTINUOUS PROCESS FOR MAKING A NON-NEWTONIAN PASTE OR CREAM LIKE MATERIAL

[75] Inventors: Rolando Catiis, Rahway; Robin S. Cabanas, Somerset; Joseph Binshtock, Brunswick, all of N.J.

[73] Assignee: Colgate-Palmolive Company, Piscataway, N.J.

[21] Appl. No.: 858,928

[22] Filed: Mar. 27, 1992

[51] Int. Cl.$^5$ .......................... A61K 7/00; A61K 7/16; A61K 7/18; A61K 9/10

[52] U.S. Cl. .......................................... 424/49; 424/52; 424/59; 424/673; 252/315.01; 252/315.1; 252/315.2; 252/315.6; 366/348; 514/769; 514/770; 514/772; 514/789; 514/944; 514/969; 514/937

[58] Field of Search ..................... 424/49-58; 252/315.01, 315.1, 315.2, 315.6; 366/348; 514/937, 944, 969

[56] References Cited

U.S. PATENT DOCUMENTS

| | | | |
|---|---|---|---|
| 2,751,328 | 6/1956 | Sanders | 424/49 |
| 3,551,559 | 12/1970 | Miles | 424/49 |
| 3,840,657 | 10/1974 | Norfleet | 424/49 |
| 3,946,108 | 3/1976 | Tomlinson et al. | 424/49 |
| 3,946,994 | 3/1976 | Mertz et al. | 366/160 |
| 4,018,426 | 4/1977 | Mertz et al. | 366/162 |
| 4,018,720 | 4/1977 | Lengyez et al. | 252/534 |
| 4,020,154 | 4/1977 | Perla et al. | 424/49 |
| 4,069,310 | 1/1978 | Harrison | 424/49 |
| 4,115,308 | 9/1978 | Guerry | 252/135 |
| 4,190,373 | 2/1980 | Zucker et al. | 366/160 |
| 4,425,322 | 1/1984 | Harvey et al. | 424/52 |
| 4,599,363 | 7/1986 | Miles et al. | 424/49 |
| 4,632,825 | 12/1986 | Ferlauto et al. | 424/52 |
| 4,701,318 | 10/1987 | Ferlauto et al. | 424/52 |
| 4,774,077 | 9/1988 | Ferlauto et al. | 424/52 |
| 4,795,630 | 1/1989 | Okouchi et al. | 424/49 |
| 5,015,409 | 5/1991 | Read et al. | 252/108 |
| 5,030,444 | 7/1991 | Hoyles et al. | 424/49 |
| 5,084,268 | 1/1992 | Thaler | 424/53 |
| 5,108,734 | 4/1992 | Colodney et al. | 424/49 |

FOREIGN PATENT DOCUMENTS 61-236717 10/1986 Japan .

OTHER PUBLICATIONS

Okochi et al. GA. 106:38270L (1986).

*Primary Examiner*—Shep K. Rose
*Attorney, Agent, or Firm*—Richard E. Nanfeldt; Robert C. Sullivan; Murray Grill

[57] ABSTRACT

A continuous process for preparing a paste or cream like material which comprises the steps of means for forming under non vacuum conditions at a temperature of 90° F. to 120° F. a first low viscosity homogenous slurry of at least one non aqueous solvent and a gelling or bodying agent; means for forming a second low viscosity homogenous slurry under non vacuum conditions at a temperature of 90° F. to 130° F., means for forming a low viscosity mixture of said first low viscosity slurry and said second low viscosity slurry by a high shear mixing under non vacuum conditions at a temperature of 90° F. to 130° F. for 0.1 to 5 seconds; means for transforming under non vacuum and non mixing conditions at a temperature of 65° F. to 120° F., said low viscosity mixture into a non Newtonian mixture; and means for deaerating said non Newtonian mixture under vacuum conditions for a period of less than 3 seconds to form said paste or cream like material.

16 Claims, 1 Drawing Sheet

CONTINUOUS PROCESS FOR MAKING A NON-NEWTONIAN PASTE OR CREAM LIKE MATERIAL

BACKGROUND OF THE INVENTION

The present invention relates to a continuous process for the manufacture of a non Newtonian paste or cream like material such as dentrice or a cosmetic.

Dentifrices such as toothpaste or dental creams are generally extrudible pastes which contain insoluble abrasives and/or polishing agents that are used in the removal of plaque, stains and other deposits from the teeth and also help in polishing the teeth.

In one well known method of manufacture of dentifrices the dentifrices during the manufacturing are subjected to high temperature and prolonged periods of vacuum. These conditions cause a loss of volatiles such as flavoring agents during the manufacturing process. The improved continuous process of the instant invention does not employ high temperatures and prolong periods of vacuum thereby minimizing the loss of volatiles as well as reducing the cost of manufacturing due to low energy input requirements. Additionally, the resultant compositions of the instant invention exhibit non-Newtonian flow characteristics have enhanced flavor, a $G'$ value over a strain range of 0.1 to 0.5 percent at 6.3 radians/second of at least about 4,000 dynes/sq. cm. and a complex viscosity over a strain range of 0.1 to 5% at 6.3 radians/second of at least about 700 pascal—seconds thereby exhibiting improved rheological properties and improved product stability.

Toothpastes can be made up by various and many well known techniques. One such technique is disclosed in U.S. Pat. No. 3,840,657 issued Oct. 8, 1974, wherein a toothpaste composition is manufactured by making a mixture of a liquid vehicle, gelling agent and polishing agent; degassing this mixture; preparing a second mixture of a synthetic organic detergent and a liquid vehicle therefore, and degassing this mixture by raising it to an elevated temperature; and finally admixing the first and second mixtures. In the manufacture of toothpastes, invariably the powdered constituents must be mixed and dispersed with the other liquid ingredients contained in the final toothpaste product. Care must be taken to remove the air in the mixing in of the powders so as to prevent the entrainment of air in the resulting paste.

Various known methods are disclosed in such standard references as "Cosmetics: Science and Technology", by Sagarin, Volume I, pages 510–511, published by Interscience Publishers, Inc. (1972). One such method is the mixing of a paste mass under vacuum to remove the entrained air. The speed of removal will generally depend on the air quantity and mixer construction. Air can also be removed by atmospheric mixing followed by the use of a continuous deaerator such as a Versator available from Cornell Machine Co. The efficiency of deaeration will again be a function of the quantity of air present in the paste mass.

U.S. Pat. No. 2,751,328 teaches a continuous or semi continuous process for the manufacture of toothpaste. The process of this patent teaches a method similar to the instant invention but differs in the means of forming the dental paste and cream in it requires the maintaining of the slurry of the components at a temperature in excess of 140° F. up to 270° F. for a residence time of 3–5 minutes with agitation. These conditions of the process of U.S. Pat. No. 2,751,328 because of the elevated temperature, residence time and agitation provide compositions which do not have improved $G'$ values, increased complex viscosities, product stability, enhanced flavor or dispersion of the particles in the composition that are comparable to the compositions of the instant invention because of the incomplete formation of the polymeric matrix.

U.S. Pat. No. 4,599,363 describes a continuous process for the manufacture of dentifrices. Like the previously described batch processes and unlike the continuous process of the instant invention this patent describes a process that employees high temperature and prolong periods of vacuum.

Accordingly, the instant improved continuous process for the manufacture of dentifrices produces dentifrices having non-Newtonian flow characteristics, enhanced flavor, and having improved rheological properties of a $G'$ value over a strain range of 0.1 to 0.5 percent at 6.3 radians/second of at least about 4000 dynes/sq. cm, more preferably at least about 5,000 dynes/sq.cm and most preferably at least about 5,500 dynes/sq. cm and a complex viscosity over a strain range of 0.1 to 0.5% at 6.3 radians/second of at least about 700 Pascal-seconds, more preferably at least 800 Pascal-seconds and most preferably at least about 900 Pascal-seconds.

SUMMARY OF THE INVENTION

The present invention relates to a continuous process for the manufacture of a non-Newtonian paste or cream high viscosity like material such as dentifrice or a cosmetic which comprises the steps of: means for forming under non vacuum conditions at a temperature of about 90° F. to 130° F., more preferably about 100° F. to 120° F. a first homogenous slurry of low viscosity of at least one non aqueous solvent which is miscible with water and a gelling agent; means for forming a second homogenous slurry of low viscosity under non vacuum conditions at a temperature of about 90° F. to 130° F., more preferably about 100° F. to 120° F. wherein the second homogenous slurry includes water and at least one additive ingredient; means for forming a Newtonian mixture of the first slurry and the second slurry by high shear mixing under non vacuum conditions at a temperature of about 90° F. to 130° F., more preferably about 100° F. to 120° F. for about 0.1 to five seconds; means for transforming the low viscosity mixture under non vacuum conditions and under condition of non agitation or non mixing at a temperature of about 65° F. to 120° F. for about 15 to 30 minutes into a high viscosity non Newtonian paste or cream like material which is subsequently deaerated under vacuum for less than three seconds to form a dentifrice which is subsequently passed through a screen pack of less than about 0.01 inches, for example, 0.007 inches.

Another object of the instant invention is to provide a non-Newtonian dentifrice, and means for deaerating and polishing the non-Newtonian dentifrice under a vacuum of about 25 inches to about 30 inches for about 0.05 to about 2 seconds to form the non-Newtonian paste or cream like material.

Accordingly, it is an object of the present invention to provide a continuous process for the manufacture of a non-Newtonian paste or cream like material having enhanced flavor and improved product stability as evidenced by a $G'$ value over a strain range of 0.1 to 0.5 percent at 6.3 radians/second of at least about 4,000 dynes/sq. cm, and a complex viscosity over a strain range of about 0.1 to 0.5 seconds at 6.3 radians/second of at least about 700 Pascal-seconds. The improvement process provides energy input savings, labor cost savings as well as forming a composition having improved non-Newtonian flow characteristics, and enhanced flavor characteristics.

DESCRIPTION OF THE PREFERRED EMBODIMENT

Figure 1:
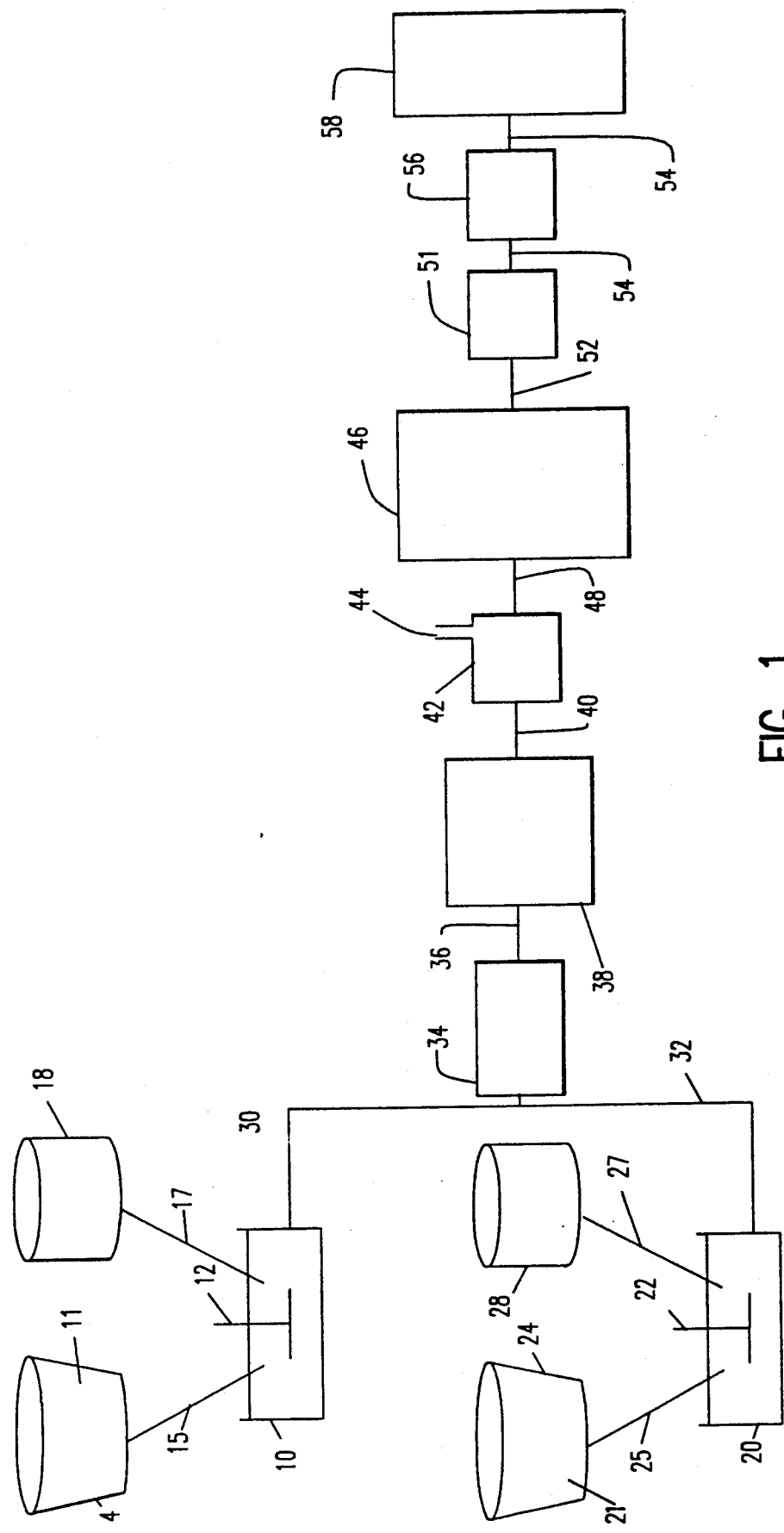
FIG. 1 illustrates a schematic flow diagram of the instant continuous process for the manufacture of an improved non-Newtonian paste or cream like material having enhanced flavor.

The present invention relates to a continuous process for the manufacture of a high viscosity non-Newtonian paste or cream like material which comprises the steps of: means for forming under non-vacuum conditions at a temperature of about 90° F. to 130° F. and more preferably about 100° F. to 120° F. a first low viscosity homogenous slurry of at least one non-aqueous solvent and a gelling agent; means for forming a second low viscosity homogenous slurry under non-vacuum conditions at a temperature of about 90° F. to 130° F., wherein the second homogenous slurry includes water and at least one additive ingredient; means for forming a low viscosity mixture of the first slurry and the second slurry by high shear mixing under non vacuum conditions and means for transforming the low viscosity mixture under non agitation conditions at a temperature of about 65° F. to 120° F. for about 15 to 30 minutes into a non Newtonian paste or cream like material, means for deaerating under vacuum for less than three seconds the non Newtonian paste or cream like material and means for filtering the non Newtonian paste or cream like material through a screen pack of less than about 0.01 inches.

The process of the instant invention is depicted in FIG. 1. A first mixer tank 10 contains a first mixing means 12 such as a stirrer. At least one first hopper 14 is supplied for solid materials 11, wherein the first hopper 14 communicates with the first mixing tank 14 through a first line 15. A first vessel 18 is supplied for the delivery of water to the first mixing tank 10, wherein the first vessel 18 communicates with the first mixing tank 10 through a second line 17. A second mixing tank 20 containing a second mixing means 22 such as a stirrer. At least one second hopper 24 is supplied for the solid gelling agent 21, wherein the second hopper 24 communicates with the second mixing tank 20 through a third line 25. A second vessel 28 is supplied for the delivery of a non aqueous solvent to the second mixing tank 20, wherein the second vessel 28 communicates with the second mixing tank 20 through a fourth line 27. Fifth 30 and sixth 32 lines are in fluid communication with the first 10 and second 20 mixing tanks respectively and the fifth 30 and sixth 32 lines are in fluid communication with an inlet of in line static mixer 34. A seventh line 36 is in fluid communication with the outlet of the in line static mixer 34 and a maturing tank 38. An eighth line 40 is in fluid communication with the maturing tank 38 and an inlet of a Versator 42 which has a vacuum means 44. The Versator 42 is in communication with a holding tank 46 through a ninth line 48, wherein the holding tank 46 is in communication with an inlet of pump 51 through a tenth line 52. A discharge line 54 has a screen pack 56 disposed therein, wherein the discharge line 54 is in communication with the outlet of pump 51. The other end of the discharge line 54 discharges into a storage tank 58. The mixing tank 20 provides the means for preparing a second low viscosity slurry of water and the solid and liquid ingredients of the cream or paste like material except for the nonaqueous solvent and gelling agent, wherein the concentration of the ingredients is about 36 to about 80 weight percent. Mixing occurs under non vacuum conditions at atmospheric conditions in the mixing tank 20 at a temperature of about 90° F. to about 130° F. for about 5 to 30 minutes at a mixing speed of about 100 to 400 rpms, more preferably about 200 to 300 rpms. The mixing tank 10 provides a means for forming a first low viscosity slurry of the non aqueous and gelling agent, wherein the concentration of the gelling agent is about 9 to 29 weight percent, more preferably about 10 to 26 weight percent. The mixing in the mixing tank 10 occurs under non vacuum conditions at atmospheric conditions for about 5 to 30 minutes at a temperature of about 90° F. to 130° F. at a mixing speed of about 100 to 400 rpms, more preferably about 200 to 300 rpms. The means for forming the low viscosity mixture of the low viscosity slurry of water and the liquid and solid ingredients and the low viscosity slurry of the non aqueous solvent and gelling agent comprises passing the two low viscosity slurry through an in line static mixer 34 under non vacuum conditions at atmospheric pressure at a temperature of about 90° F. to 130° F., wherein the residence time in the in line static mixer 34 is about 0.05 to 3.0 seconds, and more preferably about 0.05 to 2.0 seconds. The means for transforming the low viscosity mixture into a high viscosity non Newtonian mixture comprises holding the low viscosity mixture in a maturing tank 38 under non vacuum condition without mixing or agitation at a temperature of about 100° F. to 120° F. for about 15 minutes to 60 minutes more preferably about 15 to 30 minutes, under non vacuum conditions at atmospheric pressure. By employing conditions of non vacuum and non agitation or non mixing a more uniformly hydrated product with improved non Newtonian properties and less encapsulated air is formed as compared to products formed under conditions of agitation and/or vacuum. If heating and cooling and agitation is employed during the hydrating step a poorer polymeric matrix is formed, wherein there is insufficient wetting and incorporation of the solid particles into the polymeric matrix as illustrated in U.S. Pat. No. 2,751,328. A slow hydration step at an essentially constant temperature under non mixing conditions as in the instant process permits the maximization of the formation of the polymeric matrix which ensures proper wetting and incorporation of the solid particles into the polymeric matrix. The means for deaerating and polishing the non Newtonian mixture into the non Newtonian cream or paste like material having a G' value over a strain range of 0.1 to 0.5 percent at 6.3 radians/second of at least about 4,000 dynes/sq.cm, and a complex viscosity over a strain range of 0.1 to 0.5% at 6.3 radians/second of at least about 700 Pascal-seconds comprises passing the non Newtonian mixture through a Versator 42 at a temperature of about 80° F. to about 120° F. under a vacuum of about 690 to about 720 mm, wherein the residence time in the Versator 42 is about 0.05 to about 3.0 seconds, more preferably about 0.1 to about 2.0 seconds. The non Newtonian cream or paste like materials such as a toothpaste is passed through a 0.007 inch filter screen pack 56 to form the final product. The non-Newtonian cream or paste like material such as a cosmetic, toothpaste or dental cream having a G' value over a strain range of 0.1 to 0.5 percent at 6.3 radians/second of at least about 4,000 dynes/sq.cm, more preferably at least about 5,000 dynes/sq.cm, and most preferably at least about 5,500 dynes/sq. cm and a complex viscosity over a strain range of 0.1 to 0.5 percent at 6.3 radians/second of at least about 700 Pascal-seconds, more preferably about 800 Pascal-seconds and most preferably about 900 Pascal-econds comprises approximately by weight:
a) 0 to 70%, more preferably 1 to 40% of at least one non aqueous solvent;

b) 0.05 to 5.0%, more preferably 0.1 to 3.5% of at least one gelling agent, one of which gelling agents must be a crosslinked metal neutralized anionic polymer acid gelling agent;

c) 0 to 50%, more preferably 0.5 to 50%, and most preferably 0.5 to 40% of at least one polishing agent;

d) 0 to 30%, more preferably 0.5 to 25% of a bodying or swelling agent;

e) 0.05 to 3%, more preferably 0.1 to 2.5% of at least one surface active material;

f) 0 to 1.5%, more preferably 0.15 to 1.25% of a flavoring agent;

g) a fluoride containing compound in a sufficient amount to provide 0 to 5,000 ppms of fluoride ions;

h) 0 to 0.75%, more preferably 0.1 to 0.5% of a water insoluble noncationic antibacterial agent;

i) 0 to 3%, more preferably 0.1 to 2.5% of a film polymeric material;

j) 0 to 5%, more preferably 0.5 to 4% at least one anticalculus agent;

(k) 0 to 5% of an alkali metal phosphate; and (l) water.

The instant compositions show a two to five fold increase in their G' values and complex viscosities over the same formula produced by a batch process which have a G' value of 2,000 dynes/sq.cm and a complex viscosity of 400 Pascal-seconds.

In oral preparations such as a dentifrice, an orally acceptable vehicle including a water phase with a non aqueous solvent being usually present. In the present invention, the water and non aqueous solvent liquid phase usually comprises at least about 10% by weight of the oral preparation. One typical non aqueous solvent is preferably propylene glycol, which is present as a portion of the non aqueous solvent to solubilize the substantially water-insoluble noncationic antibacterial agent. The remainder of the non aqueous solvent is typically glycerine and/or sorbitol. Water is present typically in amount of at least about 3% by weight and glycerine and/or sorbitol typically total about 6.5-75% by weight of the oral preparation, more typically about 10-75%, and, together with the solubilizing non aqueous solvent, the essential non aqueous solvent components typically amount to about 7-80% by weight of the oral preparation. Reference hereto to sorbitol refers to the material typically as available commercially in about 70% aqueous solutions.

Besides the solubilizing non aqueous solvent, propylene glycol, other solubilizing agents which do not adversely affect the antibacterial activity in oral preparations may be used. These are dipropylene glycol, methyl cellosolve, ethyl cellosolve, olive oil, castor oil, amyl acetate, ethyl acetate, glycerol tristerate and benzyl benzoate.

Toothpastes, creams and gels typically contain a natural or synthetic thickener, bodying or gelling agent in proportions of about 0.1 to about 10, preferably about 0.5 to about 5%. A suitable thickener is synthetic hectorite, a synthetic colloidal magnesium alkali metal silicate complex clay available for example as Laponite (e.f. CP, SP 2002,D) marketed by Laporte Industries Limited. Laponite D analysis shows, approximately by weight, 58.00% $SiO_2$, 25.40% MgO, 3.05% $Na_2O$, 0.98% $Li_2O$, and some water and trace metals. Its true specific gravity is 2.53 and it has an apparent bulk density (g./ml. at 8% moisture) of 1.0.

Other suitable thickeners include Irish moss, i-carrageenan, gum tragacanth, starch polyvinylpyrrolidone, hydroxyethy-propylcellulose, hydroxbutyl methyl cellulose, hydroxypropyl methyl cellulose, hydroxyethyl cellulose (e.g. available as Natrosol), sodium carboxymethyl cellulose, and colloidal silica such as those available as finely ground Syloid (244) and Sylodent 15.

Organic surface-active agents are used in the compositions of the present invention to achieve increased prophylactic action, assist in achieving thorough and complete dispersion of the anticalculus agent, if present, throughout the oral cavity, and render the instant compositions more cosmetically acceptable. The organic surface-active material is preferably anionic, nonionic or ampholytic in nature, and it is preferred to employ as the surface-active agent a detersive material which imparts to the composition detersive and foaming properties. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as a sodium lauryl sulfate, alkyl aryl sulfonates such as sodium dodecyl benzene sulfonate, higher alkyl sulfoacetates, higher alkyl sulfoacetates higher fatty acid esters of 1.2 dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. The use of these sarcosinate compounds in the oral compositions of the present invention is particularly advantageous, since these materials exhibit a prolonged and marked effect in the inhibition of acid formation in the oral cavity due to carbohydrate breakdown in addition to exerting some reduction in the solubility of tooth enamel in acid solutions. Examples of water-soluble nonionic surfactants are condensation products of ethylene oxide with various reactive hydrogen-containing compounds reactive therewith having long hydrophobic chains (e.g. aliphatic chains of 12 to 20 carbon atoms), which condensation products ("ethoxamers") contain hydrophilic polyoxyethylene moieties, such as condensation products of poly (ethylene oxide) with fatty acids, fatty alcohols, fatty amides, polyhydric alcohols (e.g. sorbitan monostearate) and polypropyleneoxide (e.g. Pluronic materials).

A surface active agent is typically present in the composition in amount of about 0-5% by weight, more preferably about 0.05 to 3.5 wt. %. The surface active agent can assist in the dissolving of the noncationic antibacterial agent and thereby diminish the amount of solubilizing non aqueous solvent which is needed.

When the composition of this invention is a dental composition, the composition generally contains a dentally acceptable polishing material. Examples of polishing materials are water-insoluble sodium metaphosphate, potassium metaphosphate, tricalcium phosphate, dehydrated calcium phosphate, anhydrous dicalcium phosphate, calcium pyrophosphate, magnesium orthophosphate, trimagnesium phosphate; calcium carbonate, aluminum silicate, zirconium silicate, silica, bentonite, and mixtures thereof.

Other suitable polishing material include the particulate thermosetting resins described in U.S. Pat. No. 3,070,510 such as melamine, phenolic, and urea-formaldehyde, and cross-linked polyepoxides and polyester. Preferred polishing materials include-crystalline silica having particle sized of up to 5 microns, a mean particle size of up to 1.1 microns, and a surface area of up to 50,000 cm.$^2$/gm., silica gel or colloidal silica, and complex amorphous alkali metal aluminosilicate.

When visually clear or opacified gels are employed, a polishing agent of colloidal silica, such as those sold under the trademark SYLOID as Syloid 72 and Syloid 74 or under the trademark SANTOCEL as Santocel 100 or alkali metal almuino-silicate complexes are particularly useful, since they are consistent with gel-like texture and have refractive indices close to the refractive indices of gelling agent-liquid (including water and/or humectant) systems commonly used in dentifrices.

Many of the so-called "water-insoluble" polishing materials are anionic in character and also include small amounts of soluble material. Thus, insoluble sodium metaphosphate may be formed in any suitable manner as illustrated by Thorpe's Dictionary of Applied Chemistry, Volume 9, 4th Edition, pp. 510–511. The forms of insoluble sodium metaphosphate known as Madrell's salt and Kurrol's salt are further examples of suitable materials.

These metaphosphate salts exhibit only a minute solubility in water, and therefore are commonly referred to as insoluble metaphosphates (IMP). There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced or eliminated by washing with water if desired. The insoluble alkali metal metaphosphate is typically employed in powder form of a particle size such that no more than about 1% of the material is larger than 37 microns.

The polishing material is generally present in the dental cream paste or gel compositions in weight concentrations of 0% to 50%.

The sources of fluoride ions in dental compositions, if present, or fluorine-providing component, if present, as anti-caries as well are well known in the art as anti-caries agents. These compounds may be slightly soluble in water or may be fully water-soluble. They are characterized by their ability to release fluoride ions in water and by freedom from undesired reaction with other compounds of the oral preparation. Among these materials are inorganic fluoride salts, such as soluble alkali metal, alkaline earth metal salts, or example, sodium fluoride, potassium fluoride, ammonium fluoride, calcium fluoride, a copper fluoride such as cuprous fluoride, zinc fluoride, barium fluoride, sodium fluorosilicate, ammonium fluorosilicate, sodium fluorizirconate, sodium fluorozirconate, sodium monofluorphosphate, alaminum mono-and difluorophosphate, and fluorinated sodium calcium pyrophosphate. Alkali metal and tin fluorides, such as sodium and stannous fluorides, sodium monofluorophosphate (MFP) and mixtures thereof, are preferred.

The amount of fluorine-providing compound is dependent to some extent upon the type of compound, its solubility, and the type of oral preparation, but it must be a non-toxic amount, generally about 0.0005 to about 3.0% in the preparation. In a dentifrice preparation, e.g. dental gel and toothpaste paste or cream, an amount of such compound which releases up to about 5,000 ppm of fluoride ion by weight of the preparation is considered satisfactory. Any suitable minimum amount of such compound may be used, but it is preferable to employ sufficient compound to release about 300 to about 5,000 ppms, more preferably 800 to 2,000 ppms of fluoride ion.

Typically, in the cases of alkali metal fluorides, this component is present in an amount of 0 to 5% by weight, based on the weight of the preparation, and preferably in the range of about 0.05% to about 2.5%. In the case of sodium monofluorphosphate, the compound may be present in an amount of about 0.1 to 8%, more preferably about 0.35 to 7.6%.

The composition of the instant invention can contain an effective antiplaque amount of a substantially water insoluble noncaitonic antibacterial agent selected from the group consisting essentially of halogenated diphenyl ethers and phenolic compounds and about 0 to about 3% by weight of a synthetic anionic polymeric polycarboxylate having a molecular weight of about 1,000 to 1,000,000, wherein the non aqueous solvent includes a solubilizing agent selected from the group consisting of propylene glycol, dipropylene glycol, methylcellosole, ethyl cellosolve, olive oil, castor oil, amyl acetate, ethyl acetate, glycerol tristearate and benzyl benzoate which must be mixed with at least one of glycerine and/or sorbitol. The amount of the solubilizing agent must be sufficient to dissolve the antibacterial agent.

Typical examples of water insoluble noncationic antibacterial agents which are particularly desirable from considerations of antiplaque effectiveness, safety and formulation are:

Halogenated Diphenyl Ethers

2',4,4'-trichloro-2hydroxidiphenyl ether (Triclosan)
2,2'dihydroxy-5,5'-dibromo-diphenyl ether.

Phenolic Compounds (including phenol and its homologs, mono-and polyalkyl and aromatic halophenols, resorcinol and its derivatives, bisphenolic compounds and halogenated salicylanilides)

Phenol and its Homologs

Phenol
Methyl - Phenol
Methyl - Phenol
Methyl - Phenol
Ethyl - Phenol
2,4-Dimethyl - Phenol
2,5-Dimethyl - Phenol
3.4-Dimethyl - Phenol
2.6-Dimethyl - Phenol 4-n-Propyl - Phenol
4-n-Butyl - Phenol
4-n-Amyl - Phenol
4-Tert-Amyl - Phenol
4-n-Hexyl - Phenol
4-n-Heptyl - Phenol
Mono- and Poly-Alkyl and Aromatic Halophenols
Methyl - p-Chlorophenol
  Ethyl - p-Chlorophenol
  n-Propyl - p-Chlorophenol
  n-Butyl- p-Chlorophenol
  n-Amyl - p-Chlorophenol
  sec-Amyl - p-Chlorophenol
  n-Hexyl - p-Chlorphenol
  Cyclohexyl - p-Chlorophenol
  n-Heptyl - p-Chlorophenol
  n-Octyl - p-Chlorophenol
O-Chlorophenol
  Methyl - o-Chlorophenol
  Ethyl - o-Chlorophenol
  n-Propyl - o-Chlorophenol
  n-Butyl - o-Chlorophenol
  n-Amyl - o-Chlorophenol
  tert-Amyl - o-Chlorophenol
  n-Hexyl - o-Chlorophenol
  n-Heptyl - o-Chlorophenol
p-Chlorophenol
o-Benzyl - p-Chlorophenol
o-Benzyl m-methyl - p-Chlorophenol
o-Phenylethyl - p-Chlorophenol
o-Phenylethyl-m-methyl - p-Chlorophenol
3-Methyl - p-Chlorophenol
3.5 Dimethyl - p-Chlorophenol
6-Ethyl-3-methyl - p-Chlorophenol
6-n-Propyl-3-methly - p-Chlorophenol
6-iso-Propyl-3-methyl - p-Chlorophenol
2-Ethyl-3,5-dimethyl - p-Chlorophenol
6-sec Buty-3-methyl - p-Chlorophenol,
2-iso-Propyl -3,5-dimethyl - p-Chlorophenol
6-Diethylmethyl-3-methyl - p-Chlorophenol
6-iso-Propyl-2-ethyl-3-methyl- p-Chlorophenol
2-sec Amyl 3,5-dimethyl - p-Chlorophenol
2-Diethylmethyl-3,5-dimethyl - p-Chlorophenol
6-sec Octyl-3-methyl - p-Chlorophenol
p-Bromophenol
Methyl - p-Bromophenol
Ethyl - p-Bromophenol
n-Propyl - p-Bromophenol
n-Butyl - p-Bromophenol
n-Amyl - p-Bromophenol
sec-Amyl - p-Bromophenol
n-Hexyl - p-Bromophenol
Cyclohexyl - p-Bromophenol
o-Bromophenol
tert-Amyl - o-Bromophenol
n-Hexyl - o-Bromophenol
n-Propyl-m.m-Dimethyl - o-Bromophenol
2-Phenyl Phenol
4-Chloro-2-methyl phenol
4-chloro-3-methyl phenol
4-chloro-3,5-dimethyl phenol
4,4-dichloro-3,5-diaethyophenol
3,4,5,6-terabromo-2-methylphenol
5-methyl-2-pentylphenol
4-isopropyl-3-methylphenol
5-chloro-2-hydroxydiphenylemthane Resorcinol and its Derivatives Resorcinol
Methyl - Resorcinol
Ethyl - Resorcinol
n-Propyl - Resorcinol
n-Buryl - Resorcinol
n-Amyl - Resorcinol
n-Hexyl - Resorcinol
N-Heptyl - Resorcinol
n-Octyl - Resorcinol
n-Nonyl - Resorcinol
Phenyl - Resorcinol
Benzyl - Resorcinol
Phenylethyl - Resorcinol
Phenylpropyl - Resorcinol
P-Chlorobenzyl - Resorcinol
5-Chloro - 2,4-Dihydroxydiphenyl Methane
4'-Chloro -2,4-Dihydroxydiphenyl Methane
5-Bromo -2,4-Dihydroxydiphenyl Methane
4'-Bromo - 2,4-Dihydroxydiphenyl Methane
4'-Bromo -2,4-Dihydroxydiphenyl Methane Bisphenolic Compounds 2,2'-methylene bis (4-chlorophenol)
2.2'-methylene bis (3,4,6-trichlorophenol)
2,2'-methylene bis(4-chloro-6-bromophenol)
bis (2-hydroxy-3,5 -dichlorophenyl) sulfide
bis (2-hydroxy-5-chlorobenzyl) sulfide If a noncationic antibacterial agent is used in the dental composition, it is present in the oral composition in an effective antiplaque amount, typically about 0 to about 0.75% by weight, more preferably about 0.1 to about 0.50%. The antibacterial agent is substantially water-insoluble, meaning that its solubility is less than about 1% by weight in water at 25° C. and may be even less than about 0.1%.

The preferred halogenated diphenyl ether is triclosan. The preferred phenolic compounds are hexyl resorcinol and 2,2'-methylene bis(4-chloro-6-bromophenol). The most preferred antibacterial antiplaque compound is triclosam. Triclosan is disclosed in aforementioned U.S. Pat. No. 4,022,880 as an antibacterial agent in combination with an anticalculas agent which provides zinc ions. It is also disclosed as an antiplaque agent in a dentifrice formulated to contain a lamellar liquid crystal surfactant phase having a lamellar spacing of less than about 6.0 mm and which may optionally contain a zinc salt in published European Patent Application No. 0161898 of Lane et al and in a dentifrice containing zinc citrate trihydrate in published European Patent Application No. 0161899 to Saxton et al. Synthetic anionic polymeric polycarboxylate having a molecular weight of about 1,000 to about 1,000,000, preferably about 30,000 to about 500,000, have been used in optimizing anticalculus effectiveness of linear molecularly dehydrated polyphosphate salts, as disclosed in U.S. Pat. No. 4,627,977 to Gaffar et al. It is also effective to enhance delivery and retention of the nonionic antibacterial, antiplaque agent to dental surfaces.

The synthetic anionic polymer such as a polymeric polycarboxylate is an inhibitor of alkaline phosphatase enzyme. Synthetic anionic polymeric polycarboxylates and their complexes with various cationic germicides, zinc and magnesium have been previously disclosed as anticalculus agents per se in, for example U.S. Pat. No. 3,429,963 to Shedlovsky; U.S. Pat. No. 4,152,420 to Gaffar: U.S. Pat. No. 3,956,480 to Dichter et al; U.S.

Pat. No. 4,138,477 to Gaffar; and U.S Pat. No. 4,183,914 to Gaffar et al. It is to be understood that the synthetic anionic polymeric polycarboxylates disclosed in these several patents are operative in the compositions and process of this invention and such disclosures are to that extent incorporated herein by reference thereto.

The synthetic anionic polymeric polycarboxylates employed herein informing the gel composition are well known, being employed in the form of their neutralized water soluble alkali metal (e.g. potassium and preferably sodium) or ammonium salts. Preferred are 1:4 to 4:1 copolymers of maleic anhydride or acid with another polymerizable ethylenically unsaturated monomer, preferably vinyl ether (maleic anhydride) having a molecular weight (M.W.) of about 30,000 to about 1,000,000, most preferably about 30,000 to about 500,000. These copolymers are available for example as Gantrez AN 139 (M.W. 500,000), A.N. 119 (M.W. 250,000); and preferably S-97 Pharmaceutical Grade (M.W. 70,000), of GAF Corporation. The term "synthetic" is intended to exclude known thickening or gelling agents-comprising carboxymethylcellulose and other derivatives of cellulose and natural gums.

Other operative polymeric polycarboxylates include those disclosed in U.S. Pat. No. 3,956,480 referred to above, such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxethyl methacrylate, methyl or ethyl acrylate, isobutyl vinyl ether of N-vinyl-2-pyrrolidone.

Additional operative polymeric polycarboxylates disclosed in above referred to U.S. Pat. Nos. 4,138,477 and 4,183,914, include copolymers of maleic anhydride with styrene, isobutylene or ethyl vinyl ether, polyacrylic, polyitaconic and polymaleic acids, and sulfoacrylic oligomers of M.W. as low as 1,000, available as Uniroyal ND.2.

Suitable generally are polymerized olefinically or ethylenically unsaturated carboxylic acids containing an activated carbon-to-carbon olefinic double bond and at least on carboxyl group, that is, an acid containing an olefinic double bond which readily functions in polymerization because of its presence in the monomer molecule either in the alpha-beta position with respect to a carboxyl group or as part of a terminal methyle grouping. llustrative of such acids are acrylic, methacrylic, ethacrylic, alpha-chloroacrylic, crontonic, betaacryloxy propionic, sorbic, alpha-chlorsorbic, cinnamic, beta-styrilacrylic, muconic, itaconic, citraconic, mesaconic, glutaconic, aconitie, alpha-phenylacrylic, 2-benzyl acrylic, 2-cyclohexylacrylic, angelic, mbellic, fumaric, maleic acids and anhydrides. Other different olefinic monomers copolymeizable with such carboxylic monomers include vinylacetate, vinyl chloride, dimethyl maleate and the like. Copolymers contain sufficient carboxylic salt groups for water-solubility.

Also, useful herein are so-called carboxyvinyl polymers disclosed as toothpaste components in U.S. Pat. No. 3,980,767 to Chown et al; U.S. Pat. No. 3,935,306 to Roberts et al; U.S. Pat No. 3,919,409 to Perla et al; U.S. Pat. No. 3,911,904 to Harrison, and U.S. Pat. No. 3,711,604 to Colodney et al. They are commercially available for example under the trademarks Carbopol 934, 940 and 941 of BFGoodrich, these products consisting essentially of a collodially water-soluble polymer of polyacrylic acid crosslinked with from 0.75% to 2.0% of polyallyl sucrose of polyallyl pentaerythritol as cross linking agent.

The synthetic anionic polymeric polycarboxylate component is mainly a hydrocarbon with optional halogen and oxygen containing substituents and linkages as present in for example ester, ether and OH groups, and when present is employed in the instant compositions in approximate weight amounts of about 0.005 to about 4%, preferably about 0.05 to about 3%, more preferably about 0.1 to about 2%. Amounts in the upper portions of these ranges are typically employed in dentifrice compositions typically containing a dental abrasive and used in conjunction with brushing of the teeth, e.g. tooth pastes (including creams), gels, powders and tablets. Amounts in excess of these ranges may be employed for thickening or gelling purposes.

Without being bound to a theory, it is believed that the polymeric polycarboxylate is an anionic film forming material and is thought to attach to tooth surfaces and form a continuous film over the surfaces, thereby preventing bacterial attachment to tooth surfaces. It is possible that the noncationic antibacterial agent forms a complex with the polycarboxylate, thus forming a film of a complex of the two over tooth surfaces. The film forming property of the polycarboxylate and the enhanced delivery and film forming property of the polycarboxylate and the enhanced delivery and retention of the antibacterial agent on tooth surfaces due to the polycarboxylate appears to make tooth surfaces unfavorable for bacterial accumulation particularly since the direct bacteriostatic action of the antibacterial agent controls bacterial growth. Therefore, through the combination of three modes of actions: 1) enhanced delivery, 2) long retention time on tooth surfaces and 3) prevention of bacterial attachment to tooth surfaces, the oral composition is made efficacious for reducing plaque.

In accordance with a further aspect of the invention anticalculus properties may also be provided to the oral composition by the inclusion of a molecularly dehydrated polyphosphate salt in the compositions made by the continuous process of the instant invention.

The linear molecularly dehydrated polyphosphate salts operative herein as anticalculus agents are well known, being generally employed in the form of their wholly or partially neutralized water soluble alkali metal (e.g. potassium and preferable sodium) or ammonium salts, and any mixtures thereof. Representative examples include sodium hexametaphosphate, sodium tripolyphosphate, disodium diacid, trisodium monoacid and tetrasodium pyrophosphates and the like. Linear polyphosphates correspond to $(NaPO_3)n$ where n is about 2 to about 125. They are generally employed in the instant oral compositions in approximate weight amounts of about 0.1 to about 7%, preferably about 1 to about 7%, more preferably about 2 to about 7%. When n is at least 3 in $(NaPO_3)n$, the polyphosphates are glassy in character.

Particularly desirable anticalculus agents are tetraalkali metal pyrophosphates, including mixtures thereof, such as tetrasodium pyrophosphate, tetrapotassium pyrophosphate and mixtures thereof. An anticalculus agent comprising about 4.3% to about 7% by weight of the oral compositions is especially preferred wherein the weight ratio of tetrapotassium pyrophosphate to tetrasodium pyrophosphate is from about 4.3:2.7 to about 6:1 is especially preferred.

In order to optimize the anticalculus effectiveness of the oral composition, inhibitors against enzymatic hydrolysis of the polyphosphate can be desirably present. The synthetic anionic polymeric polycarboxylate as described is one such agent. The other is an amount of a fluoride ion source sufficient to supply about 0 to about 5,000 ppms, more preferably about 25 ppms to about 5,000 ppms of fluoride ions. The fluoride ion source may be present even when the polyphosphate anticalculus agent is not, since it also provides anticaries effectiveness.

Various other materials may be incorporated in the oral preparations of this invention made by the instant continuous process such as whitening agents, preservatives, silicones, chlorophyll compounds and/or ammoniated material such as urea, diammonium phosphate, and mixtures thereof. These adjuvants, where present, are incorporated in the preparations in amounts which do not substantially adversely affect the properties and characteristics desired. Significant amounts of zinc, magnesium and other metal salts and materials, generally soluble, which would complex with active components of the instant invention are to be avoided.

Any suitable flavoring or sweetening material may also be employed. Examples of suitable flavoring constituents are flavoring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, xylitol, sodium cyclmate, perillartine, AMP (aspartyl phenyl alanine, methyl este) saccharine and the like. Suitably, flavor and sweetening agents may together comprise from about 0.1% to about 5% or more of the preparation.

The pH of such liquid and other preparations of the invention is generally in the range of about 4.5 to about 9 to about 10 and most preferably about 6.5 to about 7.5. The pH can be controlled with acid (e.g.,citric acid or benzoic acid) or base (e.g. sodium hydroxide) or buffered (as with sodium citrate, benzoate, carbonate, or bicarbonate, disodium hydrogen phosphate, sodium dihydrogen phosphate, etc.).

The following examples are further illustrative of the nature of the present invention, but it is understood that the invention is not limited thereto. All amounts and proportions referred to herein and in the appended claims are by weight, unless otherwise indicated.

EXAMPLE 1

The following paste composition was made according to the following procedure.

|  | Weight % |
|---|---|
| Water | 21.379 |
| Dicalcium phosphate Anhydrous | 3.912 |
| Sorbitol | 12.715 |
| Sodium Monoflurophosphate | 0.758 |
| Dicalcium Phosphate (dihydrate) | 45.187 |
| Sodium Saccharin | 0.30 |
| Sodium Lauryl Sulfate | 2.328 |
| Flavor | 1.565 |
| Sodium Lauryol Sarcosinate | 0.217 |
| Glycerine | 10.759 |
| Viscarin Gelling Aent | 1.050 |

Viscarin was added into the first mixing tank 10 containing glycerine at a temperature of 70° F. and at 760 mm, and the mixture was mixed for 10 minutes to form the first low viscosity slurry.

Heated water at a temperature of 160° F. water was added to the second mixing tank 20. Sorbitol at 130° F. was added to mixing tank 20 with mixing and a blend of the sodium monofluoro- phosphate, anhydrous sodium saccharin and the sodium lauryl sulfate was also added to the mixing tank 20 to form a second low viscosity slurry and mixing at 125°-130° F. was continued for 5-10 minutes. The dicalcium phosphate was taken added to the mixing tank 20 at a temperature of 120°-125° F. and at 760 mm. The flavor was then added to the mixing tank 10 with mixing and then the sodium lauryol saccosinate was added at a temperature of 120° F. at 760 mm to the mixing tank 10 with mixing for 15-20 minutes finish forming the first low viscosity slurry.

The first and second low viscosity slurries were pumped into an in-line static mixer 34 at a temperature of 120° F. at 760 mm to form a low viscosity mixture which was then pumped into a maturing tank 38, wherein the low viscosity mixture was maintained without mixing under non vacuum conditions at a temperature of 120° F. for 30 minutes and the low viscosity mixture was transformed into a high viscosity non-Newtonian mixture.

The non Newtonian mixture was feed into a Versator 42 at a temperature of 120° F. with a vacuum of 710 mm, wherein the non Newtonian mixture was deaerated for less than three seconds and polished to form the non Newtonian paste composition. The non Newtonian was then feed through a screen pack of 0.007 inches to the holding tank.

| Test Results | |
|---|---|
| pH | 7.3 |
| Specific gravity | 1.35 |
| Complex viscosity[1] at 6.3 radians/second over a strain range of 0.1 to 0.5 percent | 1,000 Pascal seconds |
| G'[2] over a strain range of 0.1 to 0.5 percent at 6.3 radians/second | 6,000 Pascal |

[1] and [2] - Testing on Carri-Med rheometer

The same formula was made by the following batch process. Glycerine was charged into the Gel Mix Tank. Viscarin, Sodium Monofluoride Phosphate, and Sodium Saccharin were added and mixed for 5-10 minutes. Sorbitol and D.I Water (140° F.) are added to Gel mix Tank and were heated to 150°-160° F. Once at temperature, the batch was mixed for 20 minutes and then was transferred to the vacuum mixer and the cooling water was started in the jacket. Dicalcium Phosphate, Dicalcium Phosphate Anhydrous and flavor (batch temperature must be below 100° F.) were added while mixing at high speed. A vacuum (27.5" minimum) was pulled and mixing was continued for 15 minutes. The vacuum was released and the mixer was stopped and Sodium Lauryl Sulfate and Sodium Lauryol Sarcosinate were then added. A vacuum (27.5" minimum) was pulled and mixing was continued for 10 minutes. The mixer was stopped and the vacuum was released. The product was pumped through a 0.007 inch screen.

| Test Results | |
|---|---|
| pH | 7.3 |
| Specific gravity | 1.34 |

-continued

| Test Results | |
|---|---|
| Complex viscosity over a strain range of 0.1 to 0.5 percent at 6.3 radians/second | 400 Pascal seconds |
| G' over a strain range of 0.1 to 0.5 percent at 6.3 radians/second | 2,000 dynes/ sq. cm. |

What is claimed is:

1. A continuous process for preparing a non Newtonian paste or cream like material which comprises the steps of:
   (a) forming under non vacuum conditions at a temperature of 90° F. to 130° F. a first low viscosity homogenous slurry of at least one non aqueous solvent and a bodying or gelling agent;
   (b) forming a second low viscosity homogenous slurry under non vacuum condition at a temperature of 90° F. to 130° F., said second low viscosity homogenous slurry includes water and at least one additive ingredient;
   (c) forming a low viscosity mixture of said first low viscosity slurry and said second low viscosity slurry by high shear mixing under non vacuum conditions at a temperature of 90° F. to 130° F. for 0.1 to 5 seconds;
   (d) transforming said low viscosity mixture in a maturing tank under non vacuum conditions at a temperature of about 100° F. to about 120° F. for about 15 to abut 60 minutes into a high viscosity, non Newtonian mixture having less encapsulated air at atmospheric pressure and without mixing or agitation; and;
   (e) deaerating said non Newtonian mixture under vacuum conditions at a temperature of 80° F. to 120° F. for a period of 0.05 to 3 seconds to form said non-Newtonian paste or create like material.

2. A process according to claim 1, wherein at least one said additive ingredient is selected from the group consisting essentially of at least one polishing agent, an alkali metal phosphate, a polymeric material, a fluoride containing compound, a surface active compound, a flavoring agent, a bodying or gelling agent, at least one anticalculus agent, and a water insoluble noncationic antibacterial agent, and mixtures thereof.

3. A process according to claim 2, wherein said forming of said first low viscosity homogenous slurry comprises adding with mixing at 100 to 400 rpms for 5 to 20 minutes said gelling agent to said nonaqueous solvent.

4. A process according to claim 3, wherein said forming of said second low viscosity fluid comprises adding with mixing at 100 to 400 rpms for 5 to 30 minutes at least one polishing agent and at least one said other additive ingredient.

5. A process according to claim 4, wherein said forming of said homogenous low viscosity slurry comprises mixing said first low viscosity slurry with said second low viscosity slurry in an in-line static mixer.

6. A process according to claim 5, wherein said transforming of said low viscosity mixture into a non Newtonian mixture comprises holding said low viscosity mixture at atmospheric condition in a tank without mixing at a temperature of 90° F. to 120° F. for 15 to 30 minutes thereby permitting said gelling agent to hydrate and swell.

7. A process according to claim 6, wherein said deaerating of and polishing of said non Newtonian mixture comprises continuously passing said non Newtonian mixture through a Versator to form said paste or cream like material.

8. A process according to claim 7, further including passing said paste or cream like material through a screen filter.

9. A process according to claim 1, wherein said paste or cream like material comprises approximately by weight:
   (a) 1.0 to 40% of at least one said non aqueous solvent;
   (b) 0.05 to 5.0% of at least one said bodying or gelling agent;
   (c) 0.5 to 50% of at least one polishing agent;
   (d) 0 to 0.75% of a water insoluble noncationic antibacterial agent;
   (e) 0 to 5% of an anticalculus agent;
   (f) 0.05 to 3% of at least one surface active material;
   (g) 0.1 to 1.5% of a flavoring agent;
   (h) a fluoride containing compound in a sufficient amount to provide 0 to 5,000 ppms of fluoride ions;
   (i) 0 to 3% of a polymeric material;
   (j) 0 to 5% of an alkali metal phosphate;
   (k) 0 to 5% of an alkali metal phosphate; and
   (l) balance being water.

10. A process according to claim 9, wherein such gelling agent is a selected from the group consisting essentially of natural gums, synthetic gums, sodium carboxymethyl cellulose, hydroxyethyl carboxymethyl cellulose and clays and mixtures thereof.

11. A process according to claim 10, wherein said polishing agent material is selected from the group consisting essentially of calcium carbonate, crystalline silica, colloidal silica, complex alumino silicate, aluminum hydroxide, aluminum silicate, dicalcium phosphate dihydrate and silica xerogels and mixtures thereof.

12. A process according to claim 12, wherein said surface active material is a sulfate containing compound.

13. A process according to claim 12, wherein said fluoride containing compound are inorganic fluoride salts.

14. A process according to claim 13, wherein said polymeric material is a copolymer of methyl vinyl ether and maleic anhydride.

15. A process according to claim 14, wherein said alkali metal phosphate is an alkali metal pyrophosphate.

16. A process for preparing a non Newtonian paste or cream like material which comprises the step of transforming said low viscosity mixture in a maturing tank under non vacuum conditions at atmospheric pressure and without mixing or stirring at a temperature of about 100° F. to about 120° F. for about 15 to about 60 minutes into a high viscosity non Newtonian mixture; said low viscosity mixture comprising water, a non aqueous solvent and a bodying agent or a gelling agent.

* * * * *